United States Patent [19]

Cornforth

[11] Patent Number: 5,476,011
[45] Date of Patent: Dec. 19, 1995

[54] METHOD AND APPARATUS FOR ULTRASONICALLY TESTING SHEET MATERIALS USING ROTATING TEST HEADS

[75] Inventor: Alexander R. Cornforth, Nr. Kettering, England

[73] Assignee: British Steel plc, England

[21] Appl. No.: 946,432

[22] PCT Filed: Mar. 11, 1992

[86] PCT No.: PCT/GB92/00430

§ 371 Date: Nov. 13, 1992

§ 102(e) Date: Nov. 13, 1992

[87] PCT Pub. No.: WO92/16833

PCT Pub. Date: Oct. 1, 1992

[30] Foreign Application Priority Data

Mar. 13, 1991 [GB] United Kingdom .................. 9105361

[51] Int. Cl.[6] ................................................. G01N 29/26
[52] U.S. Cl. ................................ 73/641; 73/634; 73/159
[58] Field of Search .................... 73/633, 634, 619, 73/620, 627, 632, 641, 159, 621, 628, 625, 598, 597, 634, 641

[56] References Cited

U.S. PATENT DOCUMENTS

| | | | |
|---|---|---|---|
| 3,431,774 | 3/1969 | Dory et al. | 73/67.8 |
| 4,131,026 | 12/1978 | Ries et al. | 73/625 |
| 4,170,145 | 10/1979 | Kennedy et al. | 73/618 |
| 4,290,309 | 9/1981 | Charlebois et al. | 73/621 |
| 5,237,874 | 8/1993 | Latimer et al. | 73/621 |

*Primary Examiner*—Richard Chilcot
*Assistant Examiner*—Joseph L. Felber
*Attorney, Agent, or Firm*—Bacon & Thomas

[57] ABSTRACT

A method and apparatus for ultrasonically testing sheet material comprising rotating at least one ultrasonic sensor, mounted on a rotatable test head, about an axis of rotation substantially normal to the plane of the sheet material as it moves therepast.

10 Claims, 5 Drawing Sheets

METHOD AND APPARATUS FOR ULTRASONICALLY TESTING SHEET MATERIALS USING ROTATING TEST HEADS

BACKGROUND OF THE INVENTION

1. Field of the Invention

This invention relates to non-destructive testing, and more particularly to the non-destructive testing of sheet materials such as steel plate.

Non-destructive testing is one of the standard techniques for testing the quality of products and materials, and amongst the most common non-destructive testing techniques are ultrasonic testing techniques. Ultrasonic techniques may be used for detecting surface defects and/or internal defects and/or thickness variations.

Non-destructive testing of steel in sheet form such as steel plate (which may for example be of the order of 3 mm in thickness or greater) is a particularly important application of the technique, because such steel plate is the end product of the relevant steel production process, and the provision of testing on an automatic basis of the quality of the plate produced is of great utility to the manufacturer.

2. Description of the Prior Art

Known and existing methods of such automatic ultrasonic testing of sheet materials usually involves moving one or more testing heads in a straight line along the length of the material, although in an attempt to cover a greater area of the sheet material a sinusoidal path of the testing head or heads relative to a sheet of material has been proposed and used in some instances by transverse oscillation of the head as the sheet material moves therepast. A continuing problem with these previous proposals and existing methods is the limitation of coverage of the testing across the sheet material.

SUMMARY OF THE INVENTION

It is an object of the present invention to enable the provision of improved ultrasonic testing of sheet materials, particularly but not exclusively of steel plates.

According to one aspect of the present invention there is provided apparatus for ultrasonically testing sheet material comprising at least one ultrasonic sensor mounted on a rotatable test head for rotation about an axis of rotation thereof, said axis of rotation being arranged such as to be, in use, substantially normal to the mean plane of the sheet material as it moves therepast.

According to another aspect of the present invention there is provided a method of ultrasonically testing sheet material comprising rotating at least one ultrasonic sensor, mounted on a rotatable test head, about an axis of rotation substantially normal to the plane of the sheet material as it moves therepast.

In a preferred embodiment, in operation, the rotation of the test head occurs as the sheet material moves past on a continuous basis, the test head carries a plurality of sensors, and a plurality of test heads are disposed across the sheet material transverse to the direction of movement thereof. The plurality of test heads may be disposed in a staggered array of a plurality of rows.

The ultrasonic sensor or sensors may comprise devices ultrasonically connecting to the relevant surface of the sheet material by means of a free jet of contact fluid, or by means of appropriately configured contact shoes, which may additionally include provision for an intervening layer of contact fluid.

The ultrasonic sensors may comprise sheet thickness sensors and/or interior defect sensors and/or surface defect sensors.

In one embodiment of the invention a plurality of groups of four surface defect testing sensors may be spaced around the rotatable test head. The orientation of the groups of surface defect testing sensors may be at different angles to the normal to the axis of rotation of the rotatable head.

The testing sensors may be arranged such that during different parts of their rotation upon the rotatable head they are utilized for different sensing purposes. Thus, in a preferred embodiment, within a part of rotation of a predetermined angle on either side of the line of movement of the sheet of material, sensors may be used to detect interior imperfections, whilst in other parts of their rotation they may employed to measure the sheet thickness. In a particular embodiment in arcs extending for 45° on either side of the line of movement of the sheet, sensors may be used to sense internal, such as lamination, imperfections, and in arcs extending at 45° on either side of the normal to the line of movement of the sheet the same sensors may be employed to measure the thickness of the sheet.

The ultrasonic sensors proximate the edges of the sheet may be arranged during passage through the arc of their rotation adjacent the edges of the sheet to increase their scanning density, to increase the testing at this area of sheet material which is commonly particularly prone to defects of one form or another. Free-jet sensors may be arranged to detect the edge of the sheet of material by virtue of a non-coupling condition. The detection of this condition may be used to control lowering of contact shoe sensors onto the surface of the sheet adjacent the edge thereof.

In one embodiment of the invention the ratio of the speed of rotation of the rotatable test head to the linear speed of the sheet of material may be adjusted in accordance with the grade of the material being tested.

Again, in one embodiment of the invention there may be provided means for automatic grade assessment of the material, in which the information generated from the ultrasonic testing in accordance with the invention is processed automatically to enable characterization of the sheet in terms of its quality. Preferably the arrangement includes the step of pre-selecting a desired quality and thereafter determining whether the sheet has reached that quality. Additionally the arrangement may include the step that, should the sheet of material fail to reach the pre-selected quality, the grade met by the sheet is determined from data provided by the ultrasonic testing in accordance with the invention.

Yet again, in one embodiment of the invention information obtained by operation of the ultrasonic testing in accordance with the invention may be processed to generate a cutting schedule for the sheet material dependent upon quality details of the sheet across its area.

In order that the invention may be more readily understood one embodiment thereof will now be described with reference to the accompanying schematic drawings.

DESCRIPTION OF THE PREFERRED EMBODIMENT

Figure 1:
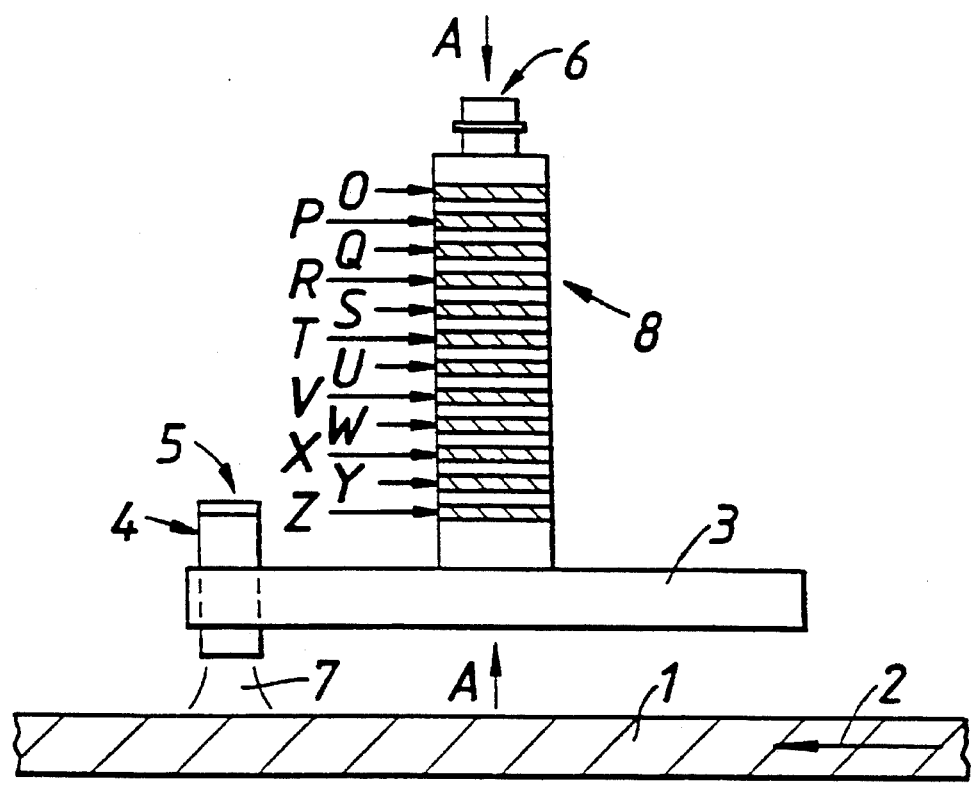
FIG. 1 is a sectional elevational view through a rotatable test head and a plate being tested.

Referring now to FIG. 1 there is shown a plate or sheet 1 of steel or other metallic material in section; the section is taken along the length of the sheet which is assumed to be travelling from right to left of the paper as shown by arrow 2. A rotating test head 3 is positioned above the plate so that it may be rotated about an axis A—A at speeds which in practice are up to 300 rotations min.$^{-1}$ and can be varied to provide more or less comprehensive testing as the quality of the plate being tested varies. Upon the rotating test head is mounted an ultrasonic sensor 4 (shown schematically). An ultrasonic transducer 5 generates in a well known manner ultrasonic impulses. A supply of water or other coupling fluid enters the rotating test head through the aperture 6 and is piped internally to the ultrasonic sensor where it emerges in a flow 7 so as to provide a continuous water path between the ultrasonic sensor and the sheet to be tested. The gap between the end of the fixed column 4 and the plate is about 10–25 mm. Ultrasonic signals are returned from the plate along the water path and are received by the transducer. The drive to and signals from the transducer are fed via slip ring O to Z shown at 8.

The ultrasonic sensors, operating in a known manner as free-jet sensors, measure the reflection of the ultrasonic pulses from the sheet and can detect both the upper surface and the lower surface, and imperfections of a laminar nature for example within the sheet being tested.

Figure 2:
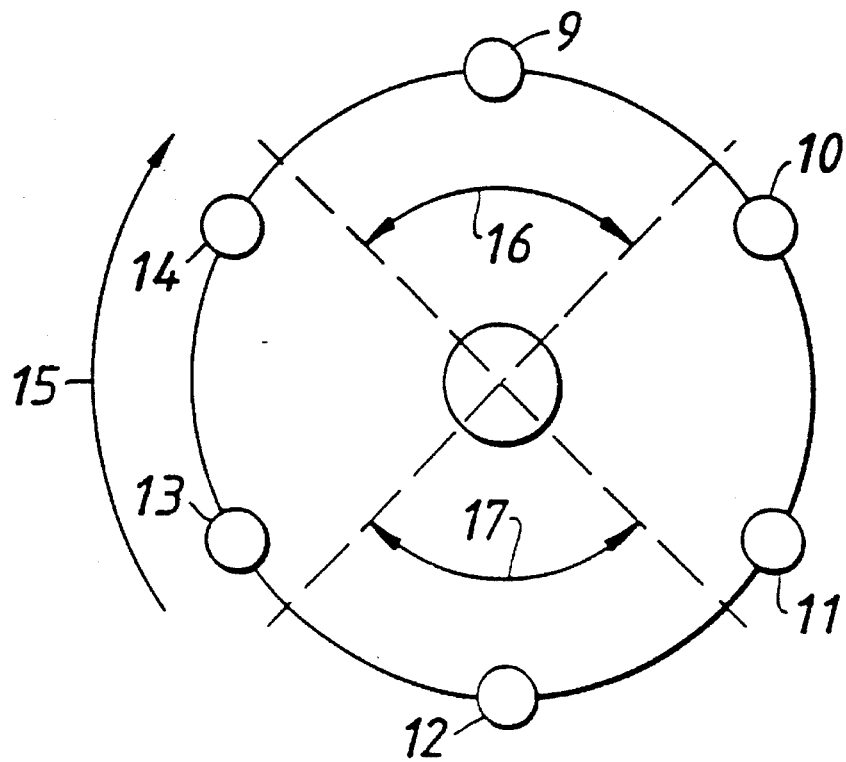
FIG. 2 is a plan view of a test head showing the scan positions of the head.

Turning now to FIG. 2 which is a plan view of a rotating test head the single ultrasonic sensor of FIG. 1 has been replaced by six ultrasonic sensors 9 to 14. These are shown spaced equidistantly around the periphery of the rotating test head and are each supplied with water of other coupling fluid and connected through slip rings for drive and signal transmission, the same as is shown in FIG. 1 for a single sensor. The rotating test head is rotating in the direction shown by the arrow 15, either above or below the plate. In practice rotation below the plate is sometimes preferred because of the ease with which the coupling waterflow may be disposed. Although each sensor may be used to measure the various parameters with a separate electronic processor and activation equipment, it is possible to switch the electronic processing and activation so that individual free-jet sensors 9 to 14 are used to detect laminar imperfections in two parts of the scan, thus enabling sharing of the sets of electronic processors and activation equipment used for this task. The laminar imperfections are detected during the phases when each sensor is in the arcs of rotation 16 and 17, and as a precaution the data obtained from each of the two arcs are processed and recorded separately so that an independent check is possible between the results.

Figure 3:
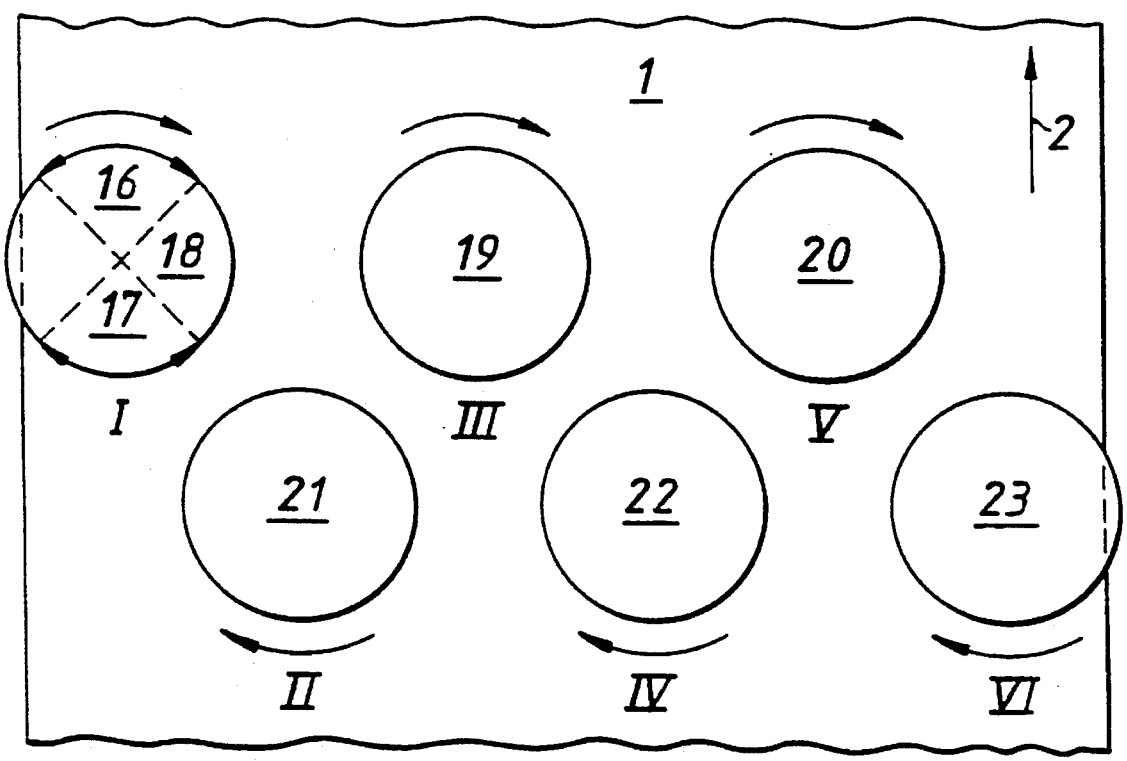
FIG. 3 shows the basic layout of an array of rotatable test heads.
Figure 4:
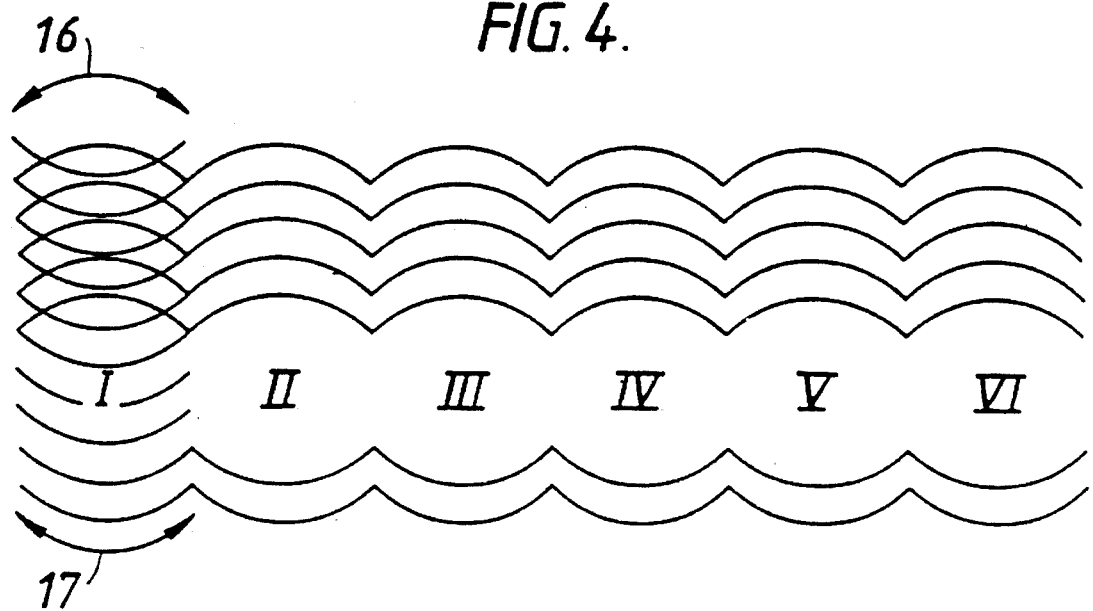
FIG. 4 shows an idealized scanning pattern on a plate.

In detecting imperfections in steel plates as has been discussed earlier, one of the problems is that of obtaining a high inspection density using a small number of heads. The rotating test head scanner so far described, although partially alleviating this problem by providing rapid continuous scanning of a portion of the surface of the plate does have disadvantages if it has to be scaled up adequately to cover right across a wide plate. Obviously its mass will increase, and the peripheral speed of the transducers will increase. For this reason the arrangement shown in FIG. 3 has been adopted in which six (in this case) rotating heads have been employed in a staggered relationship transverse the direction of movement shown by arrow 2 of the plate. Each of the rotating test heads 18 to 23 (also labelled I–VI), is employed in a manner identical to that already described in respect of a single rotating test head and as shown with reference to scanner 18 the signals from each individual ultrasonic sensor are processed during the arcs 16 and 17 to generate signals representative of the laminar imperfections in the plate during that arc of rotation. It will be appreciated that the effect of the scanning is something like that shown in FIG. 4. For simplicity the effect of the forward motion of the plate in relation to the rotation of the test heads has been ignored. This will be to distort the shape of the scan from an arcuate one, and of course, the scans shown from heads I and II will not be obtained at the same time for the same section of plate because of the stagger of the heads in the direction of the travel. However, it will be seen that ultrasonic laminar imperfection detection across the width of the plate can be achieved by suitably adjusting the recording process and by ensuring that the rotating test heads overlap in their transverse coverage of the plate.

Figure 5:
FIG. 5 shows a high density scanning pattern at a plate edge.

In FIG. 5 is shown a particularly interesting scan pattern. This represents a particularly useful scan pattern that can be achieved at the edge of the plate, an area which experience dictates should be examined particularly closely for defects. it will be seen that rotating heads 18 and 23 overlap the edges of the plate and they can be made adjustable in position so that the overlap is essentially zero. In this circumstance a scan pattern of the high density form shown in FIG. 5 can be achieved by activating the sensor during the additional arc of rotation adjacent the side of plate. In this way the rotating test heads at the edges of the plate can be used to provide additional useful high density information about the quality of the sensitive plate edges.

Figure 6:
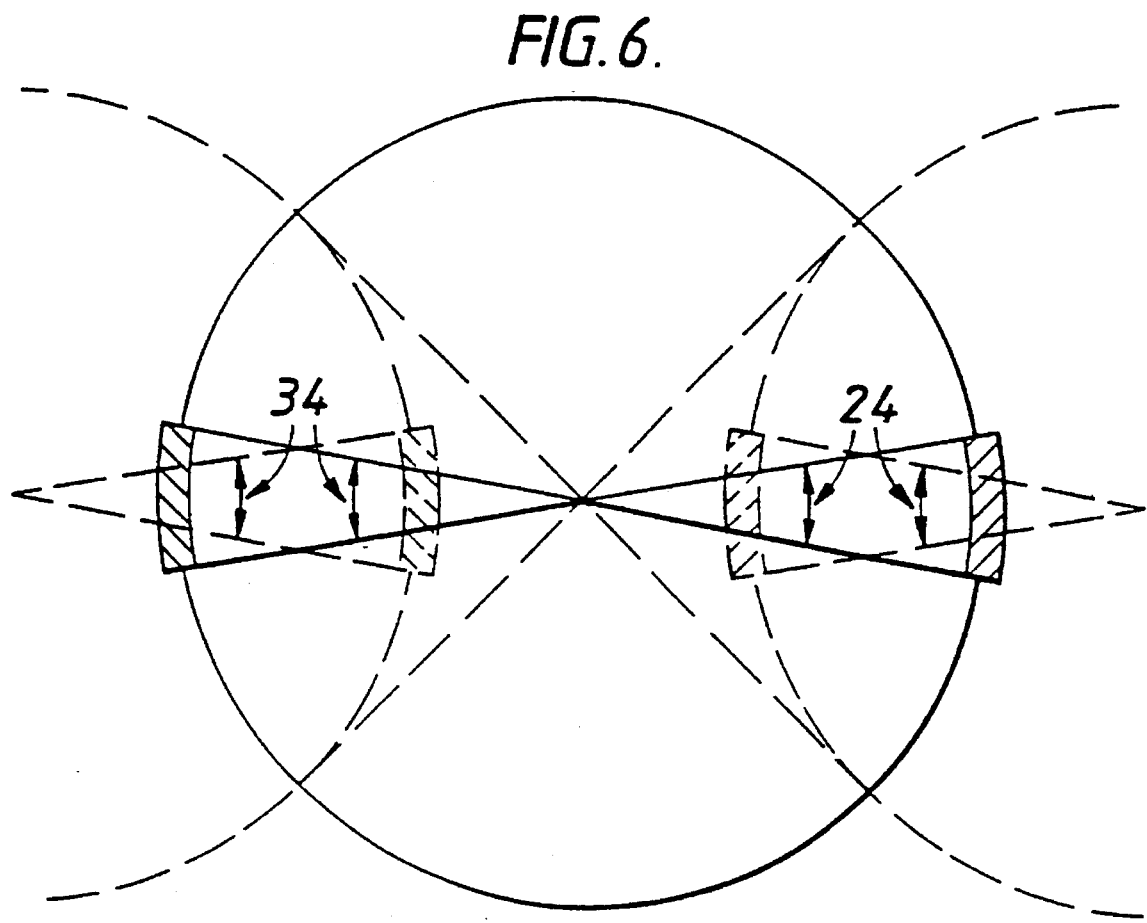
FIG. 6 shows a rotatable head employed in a thickness measuring mode.
Figure 7:
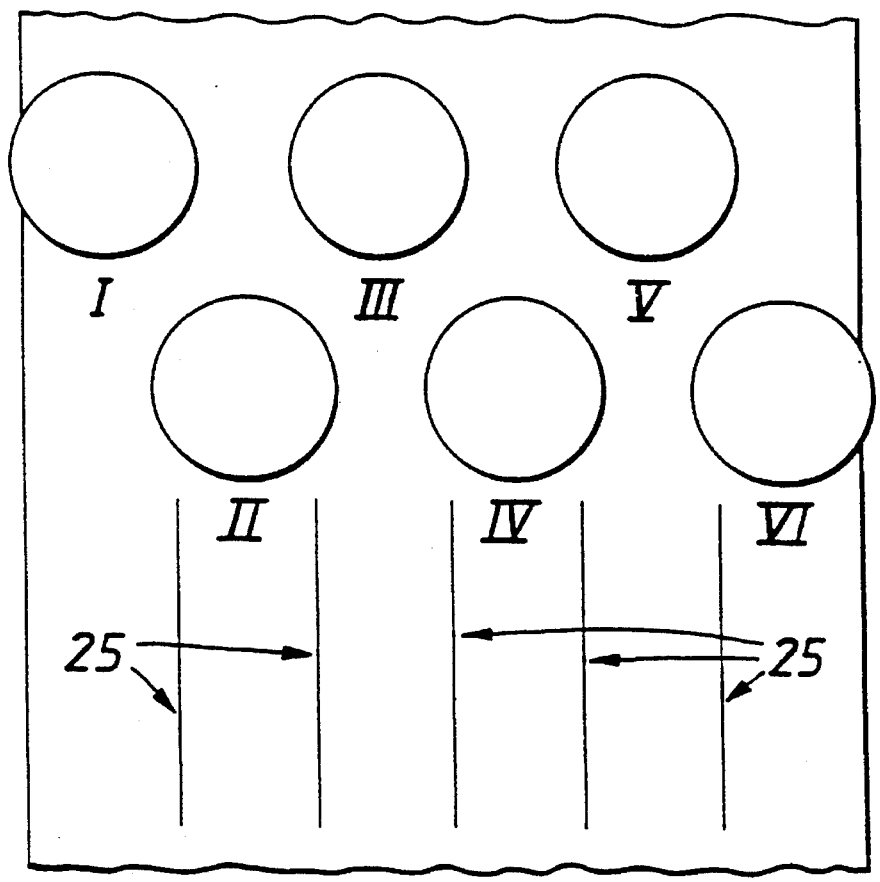
FIG. 7 illustrates thickness measurements made on plate.

Ultrasonic sensors can also be used to measure plate thickness, because a regular signal is returned from the underside or topside (as the case may be) of the plate. Since each of the ultrasonic sensors is not being used for lamination imperfection detection during at least part of its rotation, it is available to measure the thickness of the plate during these portions of the cycle. In practice the thickness of the plate does not vary rapidly or unexpectedly and therefore does not need to be monitored so frequently or at such a density as for measurements of laminar imperfections. The scan pattern 24 shown in FIG. 6, for example, covers 20° in the arc sectors not used for laminar detection. The measurements given by adjacent test heads in their adjacent arcs can be averaged and FIG. 7 shows at 25 the lines along which thickness will be monitored from six rotating test heads each sampled during the 20° arcs at the 90° position to the direction of plate travel.

So far we have considered the use of free-jet sensors mounted on the rotatable head. These sensors utilize a free jet of water for coupling and can be used because for ultrasonic waves launched vertically into the flat plate to detect thickness and laminar imperfections a free jet of water is effective. However, the second, contact-shoe, type of ultrasonic sensor is also used mounted on a rotating test head either separately, or in conjunction with free jet sensors. They can be used in a manner similar to free-jet sensors, but can also be used to detect surface defects. Their full mode of operation will not be described here, being well known in the art, but the characteristics of interest are that a compression wave launched at an angle (e.g. about 17° for steel) from the vertical into the top surface of the plate suffers mode conversion to a shear wave at that surface and travels at an angle (e.g. about 40°–45°) to the normal within the plate and reflects from the bottom and top surfaces in sequence. It will be reflected back along the path by which it came by a surface defect, and this can be detected.

Figure 8:
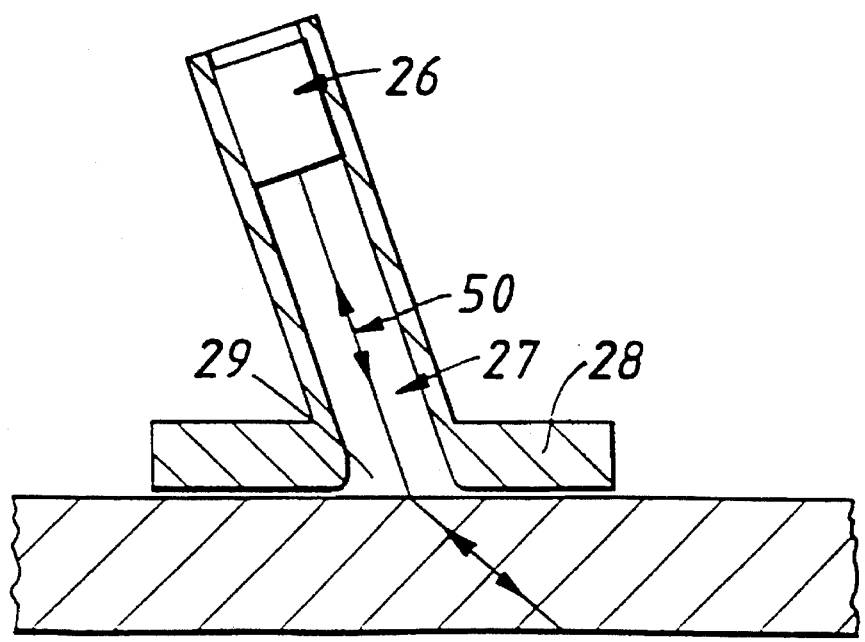
FIG. 8 is a sectional elevation of a contact shoe surface defect shear wave sensor on a rotatable test head.

Because of the angle at which the shear wave is injected into the plate the disposition of the sensor is different to that of free-jet sensors, and is shown in schematic form in FIG. 8. A ultrasonic transducer 26 launches a ultrasonic wave 50 along the coupling liquid path 27 fed with a supply of liquid piped as in the free jet example. However, in order to ensure that there is adequate coupling with the moving plate a sliding contact shoe 28 has an appropriately formed recess 29 to contain a pool of liquid to couple with the plate. As has been said these sensors are of a well known form, and so will not be described further. Conventionaly these sensors are used in quadrature, that is to say four transducers are arranged each to launch an ultrasonic shear wave into the plate through an aperture in a common contact shoe.

Figure 9:
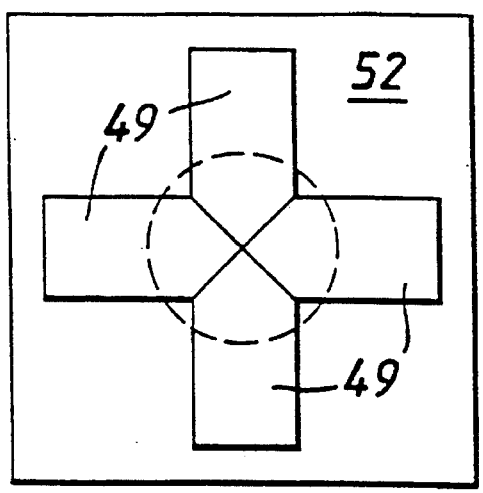
FIG. 9 is a plan view of an arrangement of four contact shoe surface defect shear wave sensors.
Figure 10:
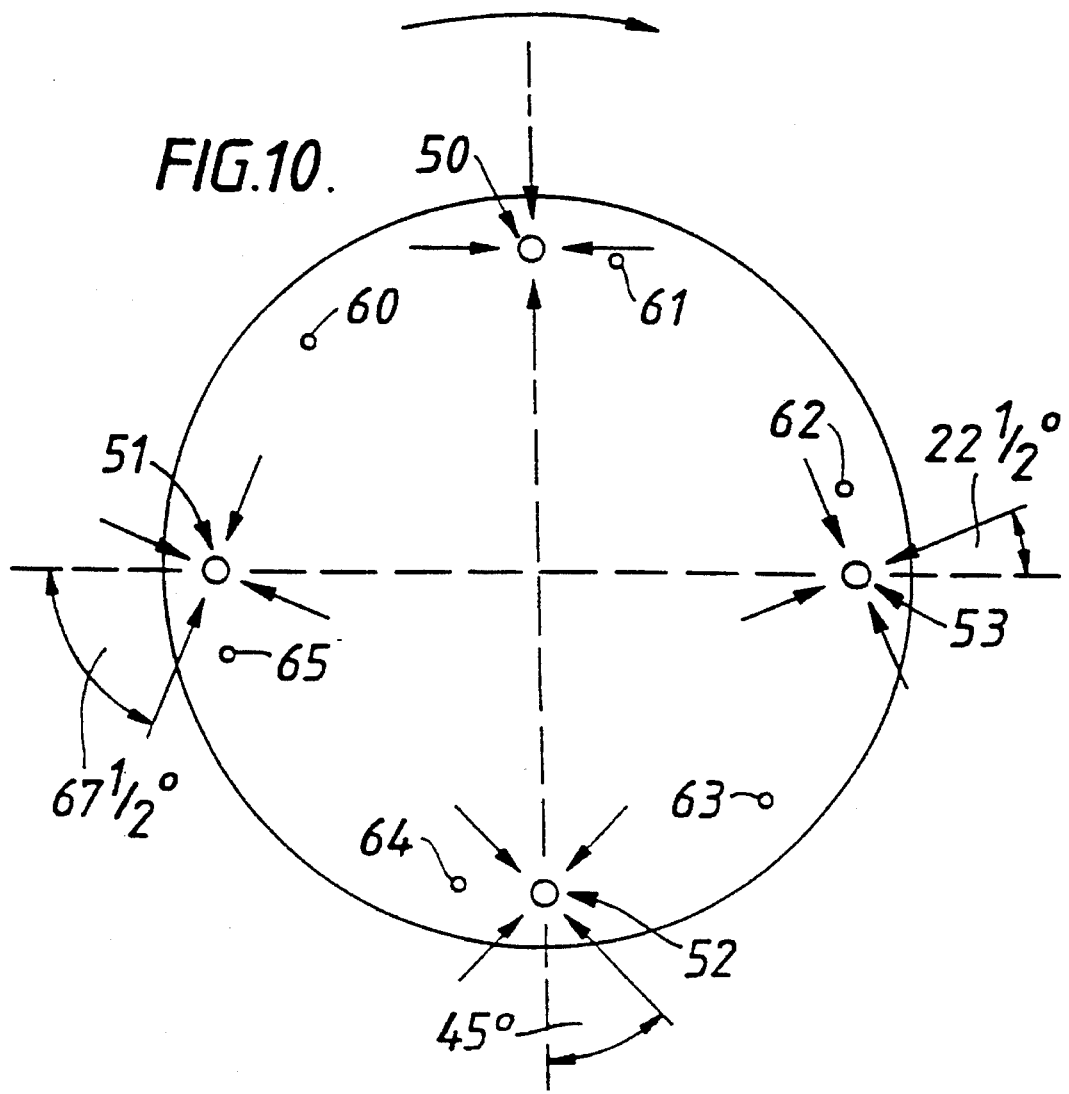
FIG. 10 shows in plan an arrangement of sixteen surface defect shear wave sensors on a rotatable test head.

This is shown in FIG. 9. Here four ultrasonic sensors 49, arranged to share one contact shoe 52, are disposed in quadrature around the shoe. These devices have been mounted on a rotating testing head as shown in FIG. 10 where the individual transducers, shown diagramatically as arrows, are arranged in groups of four at four points around the rotating head; that is at points 50, 51. 52 and 53. The individual devices of four transducers, which are placed in quadrature with the others in their group are set in the rotating head at varying angles to the local radius of the head. Number 50 is set parallel and transverse to the radius, No 52 is set at 45° to the relative position of No 50 and Nos 51 and 53 are set respectively at 221/20° forward and behind the position of No 50. Thus sixteen different directions of shear wave launch are catered for in one rotating test head so providing a rotating pattern of sixteen lines along which surface defects are sought; and as in the example shown above, with six rotating heads scanning across the plate a comprehensive monitoring of the plate condition can be obtained.

Also shown in FIG. 10 are six free jet sensors 60, 61, 62, 63, 64 and 65. And although there is no reason to limit the number to six this conveniently fits into a symmetrical arrangement on one rotating test head enabling two test methods to cover the plate comprehensively. The ultrasonic techniques used are well known, but their application on rotating test heads enables the automatic measurement of a sufficient portion of the plate to enable automatic testing of the plate quality to take place. This can be put to great advantage, in that the outputs from the sensors can be processed by electronic computing means so as to produce a numerical assessment of the quality of the plate under various parameters. The computing machine may have stored within it the range of parameters allowed for various standard qualities of plate, and it can be arranged that the plate as it passes under the rotating heads is assessed against these parameters and has the quality that it reaches indicated as it passes along the test position. A further refinement of this technique is to input into the computing means the minimum quality which a particular plate has to reach for the application for which it is intended. The plate can then be assessed, and a go/no-go signal given as to whether it is suitable for that application. In the event that the plate is not found suitable, the computing means may provide an output of the plate quality that it did meet so that it could be diverted to other applications.

Furthermore, the data assembled may allow a cutting schedule for the plate to be prepared to allow the high quality areas to be cut out separately.

The description has shown ultrasonic sensors requiring to be coupled by water or other liquid to the plate being tested. There are available ultrasonic sensors among which EMATs (Electromagnetic Acoustic Transducers) are known not requiring water coupling, although they tend to be heavy and bulky. However, in principle, these may be substituted for liquid coupling sensors if they suit the application.

In FIG. 10 there is shown a combination of free jet ultrasonic sensors and contact shoe shear wave ultrasonic sensors. It is possible to use this combination to advantage. A free-jet sensor does not touch the surface of the plate being tested and when it has no plate underneath it, either because the end of the plate has been reached or because it is running over the side edge of the plate, the sensor indicates this by a characteristic loss of coupling signal. Such loss of coupling signals can be monitored by controlling apparatus and can be used to indicate the edges and ends of the plate as they pass under the sensor. Besides being able to measure the shape and size of plate this technique can be further used to control the contact shoes of the contact shoe sensors. It can be arranged that the contact shoes are only lowered on to the plate being tested when the free jet sensors have detected that the plate is underneath the rotating test head in question.

I claim:

1. A method of ultrasonically testing sheet material comprising rotating a plurality of ultrasonic sensors mounted on and spaced about a rotatable test head about an axis of rotation substantially normal to the plane of the sheet material as it moves therepast, the testing sensors being arranged such that during different parts of their rotation upon the rotatable test head they are utilized for different testing purposes.

2. A method as claimed in claim 1 wherein the rotation of the test head occurs as the sheet material moves past on a continuing basis.

3. A method as claimed in claim 1 wherein in arcs extending for 45° on either side of the line of movement of the sheet material the sensors are used to sense for internal imperfections, and in arcs extending for 45° on either side of the normal to the line of movement of the sheet material the same sensors are employed to sense the thickness of the sheet.

4. A method as claimed in claim 1, wherein the sensors on the test head adjacent the edge of the sheet material are arranged during passage through the arc of their rotation to be adjacent to the edge to increase the scanning density.

5. A method as claimed in claim 4 wherein sensors utilizing free-jet liquid linkage to the sheet material are arranged to detect the edge of the sheet by a non-coupling condition, such detection being used to control the lowering of contact-shoe sensors onto the surface of the sheet adjacent the edge.

6. A method as claimed in claim 1 wherein the ratio of the speed of rotation of the rotatable test head to the linear speed of the sheet of material is adjustable in accordance with the quality grade of material being tested.

7. A method as claimed in claim 1 including the step of measuring a sufficient portion of a sheet material to allow automatically assessing the quality grade of the material in dependence on signal information generated from the ultrasonic testing.

8. A method as claimed in claim 7 including the step of pre-selecting a desired quality grade and thereafter determining in dependence on signal information generated from the ultrasonic testing whether the sheet of material has reached that quality grade and also including the step, upon failure of a sheet of material to reach a pre-selected quality grade, of automatically assessing the quality grade actually achieved in dependence on signal information generated from the ultrasonic testing.

9. A method as claimed in claim 1 including the step of pre-selecting a desired quality grade and thereafter determining in dependence on signal information generated from the ultrasonic testing whether the sheet of material has reached that quality grade.

10. A method as claimed in claim 1 comprising the step of measuring a sufficient portion of a sheet to allow a cutting schedule for the sheet material to be prepared that is dependent upon quality grade details of the sheet across its area.

* * * * *